United States Patent [19]

Dodge et al.

[11] Patent Number: 4,495,107

[45] Date of Patent: Jan. 22, 1985

[54] PROCESS FOR PRODUCING ALKALI METAL CYANATES

[75] Inventors: William B. Dodge, Princeton; Marc Halfon, Cranbury, both of N.J.

[73] Assignee: FMC Corporation, Philadelphia, Pa.

[21] Appl. No.: 474,216

[22] Filed: Mar. 10, 1983

[51] Int. Cl.³ ............................................... C01C 3/00
[52] U.S. Cl. ................................ 260/453 P; 423/365
[58] Field of Search ..................... 423/365; 260/453 P

[56] References Cited

U.S. PATENT DOCUMENTS

| | | | |
|---|---|---|---|
| 1,915,425 | 6/1933 | Kloepfer . | |
| 2,729,541 | 1/1956 | De Pree et al. | 423/365 |
| 2,770,525 | 11/1956 | Houpt | 23/75 |
| 2,889,198 | 6/1959 | Barrett et al. | 423/365 |
| 3,167,387 | 1/1965 | Erner | 23/75 |

FOREIGN PATENT DOCUMENTS

| | | | |
|---|---|---|---|
| 47-37615 | 9/1972 | Japan . | |
| 51421 | 5/1966 | Poland | 423/365 |
| 701941 | 12/1979 | U.S.S.R. | 423/365 |

*Primary Examiner*—John Doll
*Assistant Examiner*—Wayne A. Langel
*Attorney, Agent, or Firm*—R. L. Hansen; H. R. Ertelt

[57] ABSTRACT

An alkali metal cyanate is prepared by heating a heterogeneous mixture of urea and an alkali metal carbonate in a solvent which selectively dissolves urea, but not the alkali metal carbonate.

3 Claims, No Drawings

PROCESS FOR PRODUCING ALKALI METAL CYANATES

This invention is in the field of chemical processes; more specifically, processes for making alkali metal cyanates from urea and alkali metal carbonates.

Alkali metal cyanates traditionally have been prepared by heating, often at high temperatures, a mixture of the corresponding alkali metal carbonate and urea. See, for example, U.S. Pat. Nos. 1,915,425 and 2,770,525. If the temperature is high enough to fuse the reactants (above 500° C.), decomposition of the cyanate product to undesirable cyanide occurs. At lower temperatures the mixture is heterogeneous and reaction is incomplete. In either case, the cyanate must be recovered, milled and purified prior to its subsequent use.

It is also known to react an alkali metal carbonate with urea in a solvent. U.S. Pat. No. 3,167,387 teaches the use of a solvent which dissolves both the carbonate and urea, specifically, highly polar sulfoxides and sulfones, providing a homogeneous reaction mixture. However, that process generally employs excess urea, which remains in solution after the product alkali metal cyanate has crystallized.

It is often desired to utilize the cyanate to produce an alkyl isocyanate be reacting the cyanate with a dialkylsulfate, e.g., as disclosed in Japanese Patent 72-37615. The unreacted urea makes it undesirable to add the dialkylsulfate directly to the reaction mixture produced according to U.S. Pat. No. 3,167,387, since the contaminant urea would itself react with the alkyl isocyanate. Thus, it would be necessary to recover and purify the cyanate prepared according to U.S. Pat. No. 3,167,387 before it could be reacted with the dialkylsulfate. This is a time-consuming and costly extra step.

Therefore, it is an object of this invention to provide a process whereby an alkali metal carbonate and urea are reacted to produce an alkali metal cyanate in a state suitable, without recovery or purification, for in situ reaction with a dialkyl sulfate to produce an alkyl isocyanate.

In achieving this objective, this invention provides a process for making an alkali metal cyanate by heating urea with an alkali metal carbonate in a solvent which selectively dissolves the urea, but not the alkali metal carbonate, the reaction mixture being heterogeneous.

Generally speaking, any solvent which is chemically inert and does not appreciably dissolve the alkali metal carbonate, but does dissolve urea, is suitable. Such solvents include 1,2-dichlorobenzene, benzonitrile, 2-phenylbutane, and mesitylene. Since the reaction is preferably conducted in the temperature range 130° to 180° C., solvents having boiling points in that range, preferably above 150° C., are preferred. Among the aforesaid specifically named solvents, 1,2-dichlorobenzene is desirable, especially if it is intended to further react the alkali metal cyanate product with a dialkylsulfate.

The relative amounts of the reactants are governed by the following chemical equation:

$$M_2CO_3 + 2CON_2H_4 \rightarrow 2MOCN + 2NH_3 + CO_2 + H_2O$$

where M is an alkali metal, e.g., lithium, sodium, potassium, and rubidium, with sodium being preferred. On the basis of the stoichiometry, two equivalents of urea are required for each equivalent of alkali metal carbonate. In the process of this invention, if either reactant is in excess, it is preferred that the alkali metal carbonate be in stoichiometric excess, i.e., up to about 20%.

The production of alkali metal cyanate is preferably carried out by adding the reactant urea and alkali metal carbonate, together with the solvent, to the reactor before heating is begun, since improved yields are generally obtained thereby. The heterogeneous mixture is then heated, typically under reflux, until the evolution of gaseous by-products ceases. Upon cooling, the crystalline sodium cyanate may be recovered by filtration.

Alternatively, the cooled heterogeneous reaction mixture may be reacted directly with a dialkylsulfate, e.g., dimethylsulfate, according to the procedure described in Japanese Patent 72-37615, to produce the corresponding alkyl isocyanate, e.g., methyl isocyanate. Methyl isocyanate has many uses; for example, it is employed in the manufacture of carbofuran, a pesticide.

A better understanding of this invention will be achieved be reference to the following Examples.

EXAMPLE 1

During a one hour period a stirred mixture of urea (60 g, 1.0 mole) and sodium carbonate (63 g, 0.60 mole) in 1,2-dichlorbenzene (300 g) was heated to reflux. While the reaction mixture was heating, water vapor, ammonia and carbon dioxide evolved and were vented to the atmosphere. The reflux temperature, 177° C., was maintained for 2.6 hours, after which the heat was removed and the reaction mixture allowed to cool to room temperature. The cool mixture was filtered and the filter cake dried at 60° C. under reduced pressure for approximately two hours to yield sodium cyanate (74.51 g, 87.5% yield).

EXAMPLE 2

During a one hour period a stirred mixture of urea (60 g, 1.0 mole) and sodium carbonate (63 g, 0.60 mole) in 1,2-dichlorobenzene (300 g) is heated to reflux. While the reaction mixture is heating, water vapor, ammonia and carbon dioxide evolve and are vented to the atmosphere. Reflux is maintained for an additional two hourse, and approximately 30 ml of solvent is then distilled from the reaction mixture to remove any remaining water. Dimethyl sulfate (117 g, 0.928 mole) is added dropwise to the refluxing mixture over a one hour period. The methyl isocyanate (b.p. 40° C.) is collected by fractional distillation as it is produced.

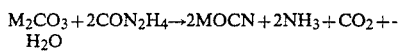

What is claimed is:

1. A process for making an alkyl isocyanate which comprises (1) first heating urea with a stoichiometric excess of alkali metal carbonate in the temperature range 130°–180° C. in a solvent which selectively dissolves the urea but not the alkali metal carbonate and is selected from the group consisting of 1,2-dichlorobenzene, benzonitrile, 2-phenylbutane and mesitylene and then (2) reacting the alkali metal cyanate produced thereby, without recovery or purification, in situ with a dialkylsulfate, thereby yielding the desired alkyl isocyanate.

2. The process of claim 1 wherein sodium carbonate is first heated with urea producing sodium cyanate, which is then reacted with dimethylsulfate, yielding methyl isocyanate.

3. The process of claim 2 wherein said solvent is 1,2-dichlorobenzene.